United States Patent [19]

Merrick et al.

[11] Patent Number: 4,581,940
[45] Date of Patent: Apr. 15, 1986

[54] DOME AND TRANSDUCER WITH COMPENSATING TEMPERATURE COEFFICIENT

[75] Inventors: Edwin B. Merrick, Stow; Thomas P. Stephens, Boxford, both of Mass.

[73] Assignee: Hewlett-Packard Company, Palo Alto, Calif.

[21] Appl. No.: 668,608

[22] Filed: Nov. 6, 1984

[51] Int. Cl.$^4$ ............................................. G01L 19/04
[52] U.S. Cl. ...................................... 73/708; 128/675
[58] Field of Search ................. 73/708, 726, 727, 725, 73/719, 720, 721; 128/675, 673; 338/3, 7, 9, 10

[56] References Cited

U.S. PATENT DOCUMENTS 4,300,395 11/1981 Shirouzu et al. ....................... 73/708
4,333,349 6/1982 Mallon et al. ......................... 73/708

Primary Examiner—Donald O. Woodiel
Attorney, Agent, or Firm—Donald N. Timbie

[57] ABSTRACT

The temperature coefficient of the combination of a transducer and any one of a plurality of disposable plastic domes manufactured to given specifications is reduced by making the temperature coefficient of the transducer have a slope that is equal and opposite to the slope of the temperature coefficient of the average dome.

4 Claims, 2 Drawing Figures

DOME AND TRANSDUCER WITH COMPENSATING TEMPERATURE COEFFICIENT

BACKGROUND OF THE INVENTION

Transducers used for measuring fluid pressure generally include a pressure responsive surface to which the pressure is applied, an electrical impedance that is mechanically coupled to the surface so as to vary in value with the pressure, and a bridge circuit that is imbalanced by an amount depending on the value of the impedance so as to produce an output signal indicative of the fluid pressure. In order to reduce variations in the output signal that can result from changes in temperature, i.e., in order to minimize the temperature coefficient, it has been customary to include adjustable temperature responsive impedances in the bridge circuit. When an integral means is used to conduct the fluid pressure being measured to the pressure sensitive surface of the transducer, the temperature responsive impedances can be adjusted so as to make the temperature coefficient of the combination have a zero value. In measuring blood pressure, however, this is disadvantageoue because all surfaces in contact with the fluid must be sterilized before the blood pressure of another patient can be measured. In order to avoid the expense involved by this procedure, it has been customary to use an inexpensive plastic means known as a "pressure dome" to conduct the blood pressure to the pressure sensitive surface of the transducer and dispose of it after the measurement of the blood pressure for each patient is concluded. It is common practice to adjust the temperature coefficient of the transducer alone to zero so that the effect of the disposable dome is not compensated. The savings resulting from the use of disposable plastic dome would be more than offset if an adjustment for minimizing the temperature coefficient were made for each dome. Thus, in the present state of the art, the measurement of blood pressure would require a permanent pressure dome that must be sterilized after each use or an inexpensive disposable plastic pressure dome that is not temperature compensated. Another alternative is to design the transducer and plastic disposable pressure dome such that the average dome produces a temperature coefficient that is close to zero, but this is difficult to do.

BRIEF SUMMARY OF THE INVENTION

In accordance with this invention, inexpensive disposable domes can be used and nearly zero temperature coefficients obtained with each by noting the change in temperature coefficient caused by the average dome and changing the temperature coefficient of each transducer by the negative of this same amount at the factory. Thus, for example, if the average dome changes the temperature coefficient of a transducer by −0.21 mm of mercury for each increase in temperature of one degree Centigrade, the temperature coefficient of the latter is adjusted to +0.21 so that the temperature coefficient of that transducer with the average dome is zero. The departure from a temperature coefficient of zero depends on the spread in the change in the temperature coefficient produced by the domes, and experience has shown that this can be kept within a range of ±0.1 mm Hg/deg C.

GRAPH A represents the temperature coefficient of a transducer without a dome and without temperature compensation;

GRAPH B represents the temperature coefficient of a transducer with a dome and without temperature compensation;

GRAPH C represents the temperature coefficient of a transducer without a dome and with temperature compensation; and GRAPH D represents the temperature coefficient of a transducer with a dome and with temperature compensation.

DETAILED DESCRIPTION OF THE INVENTION

Figure 1:
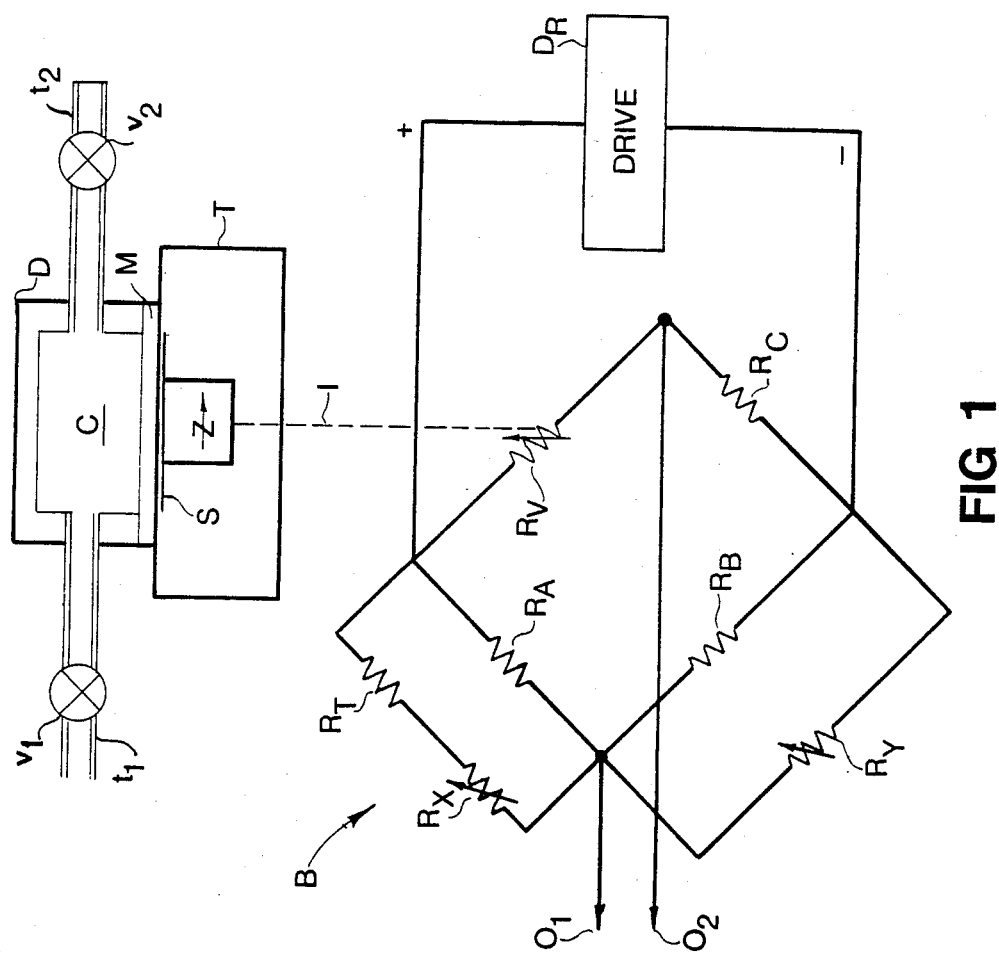
FIG. 1 is a schematic illustration of a pressure measuring system incorporating this invention.

A pressure measuring system incorporating the invention is shown in FIG. 1. It is comprised of a dome D, a transducer T and a bridge circuit B. The dome D has a cavity C formed therein that is sealed off by a membrane M. Tubes $t_1$ and $t_2$ respectively communicate with the cavity C via valves $v_1$ and $v_2$. In order to fill the cavity C with fluid from a source whose pressure is to be measured, both valves $v_1$ and $v_2$ are opened and fluid is introduced through the valve $v_1$ until it overflows from the tube $t_2$, at which point $v_2$ is closed. In measuring the blood pressure of a patient, however, a catheter is connected to $t_1$ via a "T" connection, not shown. A saline solution is introduced through the stem of the T so as to flow toward the open end of the catheter and toward the cavity C. When the saline solution overflows from $t_2$, the valve $v_2$ is closed. The purpose of the valve $v_1$ is to permit a zero or ambient pressure reading to be attained by closing $v_1$ and opening $v_2$.

When the dome D is properly attached to the transducer T, its membrane M is in intimate contact with an active surface S of the transducer T so that variations in the pressure of the fluid in the cavity C are applied to a pressure responsive impedance Z contained in the transducer T. Variations in the value of Z can be coupled as indicated by the dashed line in any way so as to produce corresponding variations in the value of one or more of the resistive impedances $R_V$, $R_A$, $R_B$ and $R_C$ of a bridge B and cause an imbalance therein. In FIG. 1, the variations in Z cause a variation in the resistor $R_V$. If Z is a pressure-responsive resistor, it can actually be the resistor $R_V$; but if the pressure-responsive impedance Z is a capacitor, it can be coupled via a suitable circuit that causes the value of $R_V$ to vary as the value of the capacitor varies. Such a circuit is described and claimed in my U.S. patent application Ser. No. 06/621,402, filed on June 18, 1984, and entitled "AGC Circuit".

In the particular embodiment of the invention shown in FIG. 1, the positive side of a drive voltage DR is connected to the junction of $R_A$ and $R_V$ and the negative side is connected to the junction of $R_B$ and $R_C$. A series circuit formed by a resistor $R_T$ that increases in value with temperature and a variable resistor $R_X$ is connected in shunt with $R_A$; and a variable resistor $R_Y$ is connected in shunt with $R_B$. One output line $O_1$ is connected to the junction of $R_A$ and $R_B$; and the other output line $O_2$ is connected to the junction of $R_V$ and $R_C$. Assume that the values of $R_A$, $R_B$, $R_C$ and the zero pressure value of $R_V$ are equal.

As described in my U.S. patent application Ser. No. 06/640,064, filed on Aug. 31, 1984 and entitled "Method of Adjusting a Temperature Compensating Resistor While It Is in a Circuit", the variable resistor $R_X$ can be a resistor formed by thick film techniques and its value can be adjusted by trimming it with a laser. In either case, the value of $R_X$ has a nominal value resulting from the manufacturing process that may vary slightly from transducer to transducer; but even if it varies considerably, it does not matter. $R_Y$ can be trimmed in the same way so as to restore balance to the bridge.

Figure 2:
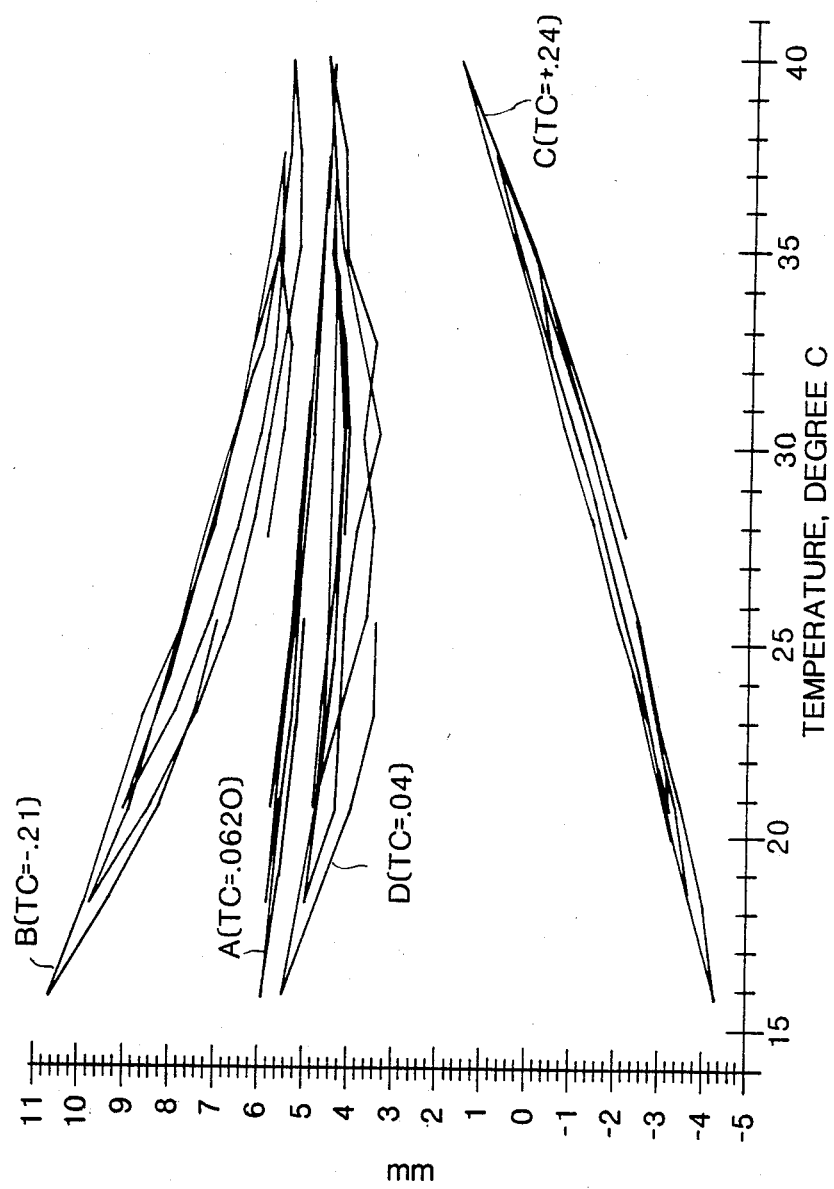
FIG. 2 contains a series of graphs that respectively illustrate the following temperature coefficients.

By way of example, if a transducer with $R_X$ at a nominal value exhibits a temperature coefficient of $-0.062$ as shown in the graph A of FIG. 2 and the effect of the average dome as determined by testing a statistical number of domes is to change the temperature coefficient of a transducer by $-0.21$ as shown by the graph B of FIG. 2, the temperature coefficient of the transducer T is adjusted with $R_X$ until it becomes 0.24, as indicated by the GRAPH C. This brings the temperature coefficient of an average dome and the particular transducer nearly to zero. (NOTE: It would be better to use graphs in which it is actually zero.) It will be noted that all the graphs exhibit a negligible amount of hysteresis about which nothing can be done.

What is claimed is:

1. A transducer that exhibits a temperature coefficient of nearly zero when used with any one of a series of domes of the same design, said transducer having
   a pressure responsive impedance,
   a bridge circuit having temperature compensating means, said bridge circuit being coupled to said pressure responsive impedance so as to be imbalanced by an amount depending on the value of said pressure responsive impedance, and
   said temperature compensating means being adjusted so that the temperature coefficient of said transducer without a dome is changed by an amount that is opposite to the change in temperature coefficient caused by the average dome.

2. Apparatus as set forth in claim 1 wherein the temperature coefficients have opposite slopes.

3. Apparatus for translating fluid pressure into an electrical signal, comprising
   a bridge circuit,
   a transducer coupled to the bridge circuit so as to imbalance it in accordance with the pressure applied to the transducer,
   a dome for applying fluid pressure to the transducer when attached thereto,
   said bridge circuit having temperature compensating means for causing the combination of the bridge circuit and transducer when the dome is not attached to the transducer to exhibit a temperature coefficient that tends to compensate for the temperature coefficient that exists when the dome is attached to the transducer.

4. Apparatus for translating fluid pressure into an electrical signal, comprising
   a transducer that varies an electrical impedance in accordance with fluid pressure applied to a surface thereof,
   an output circuit coupled to said impedance, said output circuit producing an electrical signal having a parameter that varies in response to variations in the value of said impedance,
   a dome coupled to said transducer so that the pressure of fluid contained within it is applied to said surface,
   said dome introducing a temperature coefficient of one sign; and
   said output circuit introducing a temperature coefficient of the opposite sign so as to tend to compensate for the change in temperature coefficient introduced by an average dome.

* * * * *